US010180421B2

(12) United States Patent
Johnson et al.

(10) Patent No.: US 10,180,421 B2
(45) Date of Patent: Jan. 15, 2019

(54) METHODS AND SYSTEMS TO COLLECT A BIOLOGICAL SAMPLE

(71) Applicant: BOSTON MICROFLUIDICS, Boston, MA (US)

(72) Inventors: Brandon T. Johnson, Sommerville, MA (US); Kate E. Christian, Cambridge, MA (US); Glenn H. Verner, Powell, OH (US); Daniel Morgan, Salem, MA (US)

(73) Assignee: BOSTON MICROFLUIDICS, Boston, MA (US)

( * ) Notice: Subject to any disclaimer, the term of this patent is extended or adjusted under 35 U.S.C. 154(b) by 0 days.

(21) Appl. No.: 13/945,900

(22) Filed: Jul. 19, 2013

(65) Prior Publication Data

US 2014/0050620 A1 Feb. 20, 2014

Related U.S. Application Data

(63) Continuation-in-part of application No. 13/854,718, filed on Apr. 1, 2013.

(60) Provisional application No. 61/618,195, filed on Mar. 30, 2012, provisional application No. 61/672,854, filed on Jul. 18, 2012.

(51) Int. Cl.
| | |
|---|---|
| *A61B 5/15* | (2006.01) |
| *G01N 33/50* | (2006.01) |
| *G01N 1/38* | (2006.01) |
| *B01L 3/00* | (2006.01) |
| *A61B 5/00* | (2006.01) |
| *A61B 5/145* | (2006.01) |

(52) U.S. Cl.
CPC ......... *G01N 33/50* (2013.01); *A61B 5/15003* (2013.01); *A61B 5/150236* (2013.01); *A61B 5/150251* (2013.01); *A61B 5/150748* (2013.01); *A61B 5/150755* (2013.01); *B01L 3/502* (2013.01); *G01N 1/38* (2013.01); *A61B 5/145* (2013.01); *A61B 5/150221* (2013.01); *A61B 5/150343* (2013.01); *A61B 5/706* (2013.01); *B01L 2300/0832* (2013.01); *B01L 2300/0838* (2013.01); *B01L 2400/0406* (2013.01); *B01L 2400/0478* (2013.01)

(58) Field of Classification Search
CPC .............................................. B01L 2400/0406
See application file for complete search history.

(56) References Cited

U.S. PATENT DOCUMENTS

| | | | |
|---|---|---|---|
| 3,767,085 A | | 10/1973 | Cannon et al. |
| 4,185,628 A | | 1/1980 | Kopfer |
| 4,257,267 A | | 3/1981 | Parsons |
| 4,386,606 A | * | 6/1983 | Tretinyak et al. ............ 604/220 |
| 4,915,695 A | | 4/1990 | Koobs |
| 5,013,667 A | * | 5/1991 | Lynn et al. .................. 436/126 |
| 5,339,830 A | * | 8/1994 | Blake, III .......... G01N 33/4905 422/73 |

(Continued)

*Primary Examiner* — Paul S Hyun
(74) *Attorney, Agent, or Firm* — VLP Law Group, LLP

(57) ABSTRACT

Sample processing methods and systems to collect a biological sample. A device may be configured collect a predetermined volume of a sample in sample chamber, and seal the chamber upon activation. The device may be further configured to mix the mix the sample with a predetermined volume of a reagent and/or mix the sample and the reagent in a pre-determined ration.

26 Claims, 13 Drawing Sheets

(56) References Cited

U.S. PATENT DOCUMENTS 7,435,237 B2 10/2008 Tan
2006/0228259 A1* 10/2006 Samsoondar .............. 422/82.05

* cited by examiner

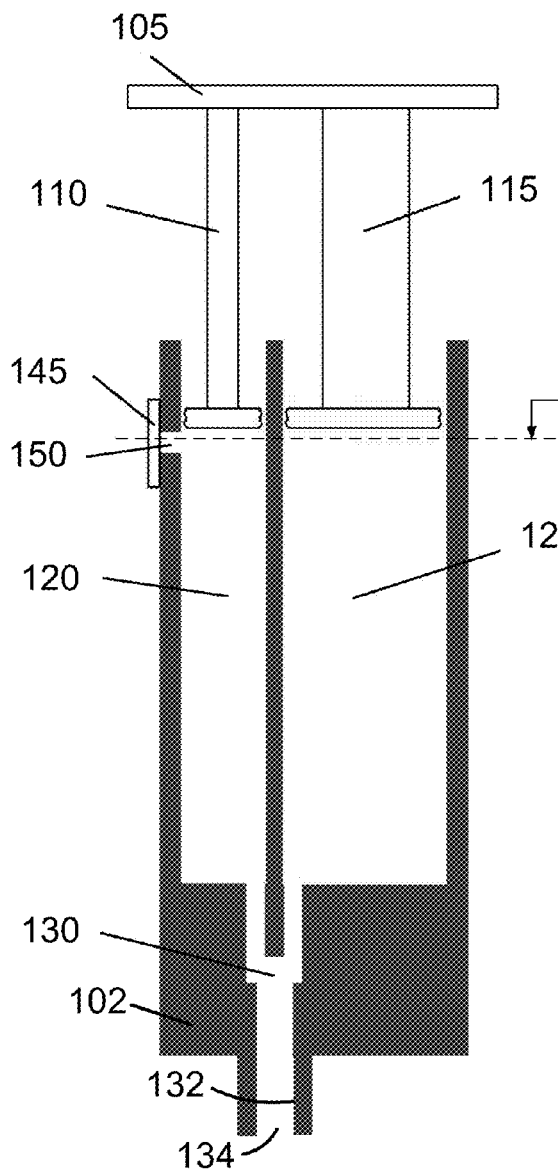
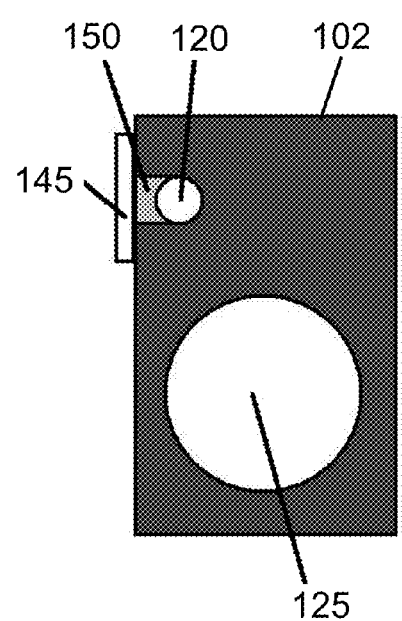
FIG. 1A
(View 1B)
FIG. 1B (View 2C)

(View 3B)

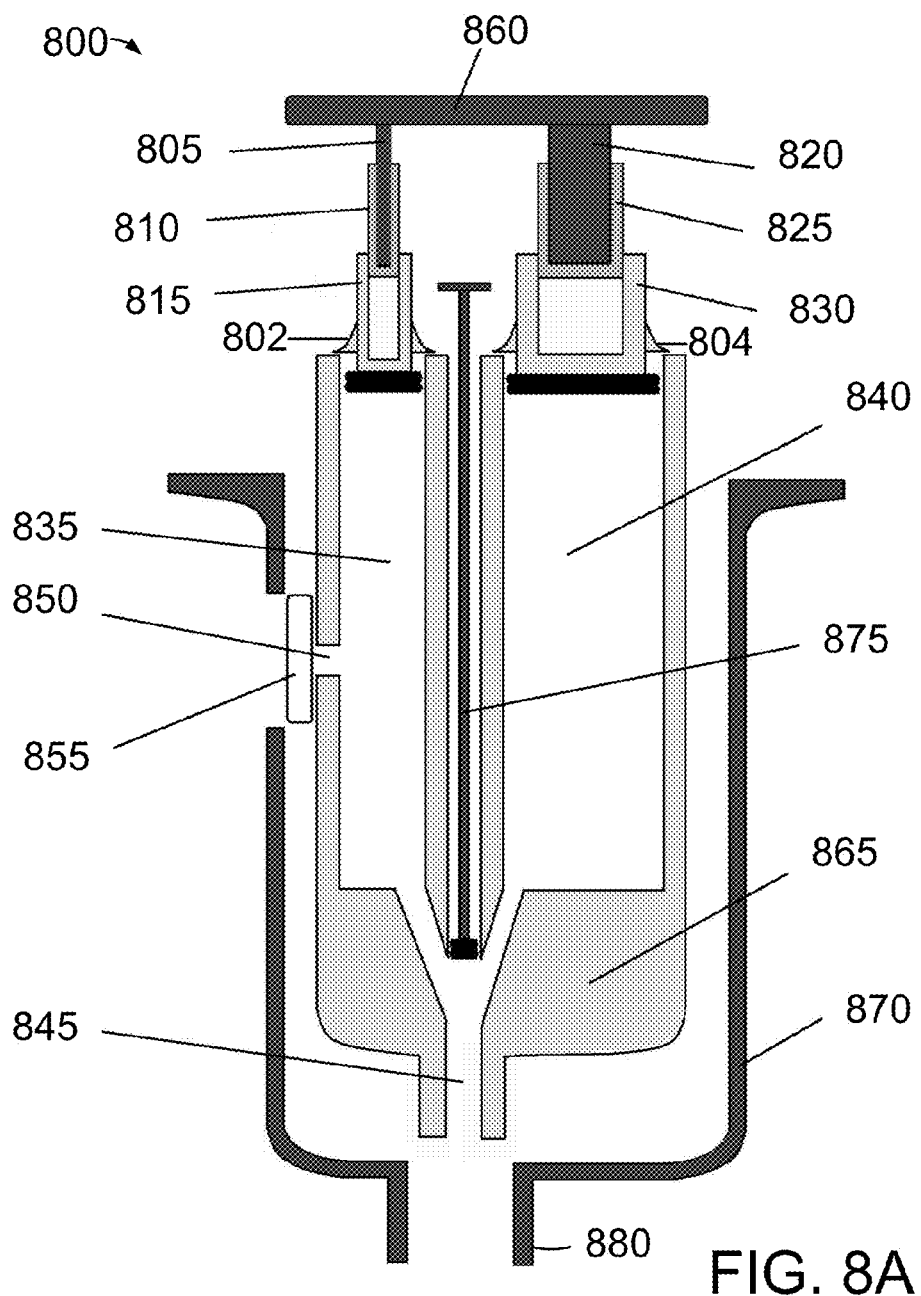
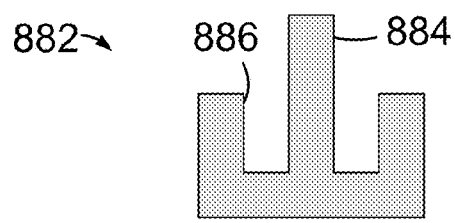
FIG. 8A
FIG. 8B

METHODS AND SYSTEMS TO COLLECT A BIOLOGICAL SAMPLE

RELATED APPLICATIONS

This application claims the benefit of U.S. provisional patent application No. 61/672,854, filed Jul. 18, 2012, and is a continuation-in-part of U.S. utility patent application Ser. No. 13/854,718, filed Apr. 1, 2013, which claims the benefit of U.S. provisional patent application No. 61/618,195, filed Mar. 30, 2012, all of which are incorporated herein by reference in their entireties.

BACKGROUND

Conventional devices to collect a biological sample are generally not portable or mechanically actuated.

Conventional devices to collect and/or process a biological sample generally do not have an internally automated collecting and measuring system visible to a user.

BRIEF DESCRIPTION OF THE DRAWINGS/FIGURES

FIG. 1A is a cut-away side-view of a sample processing device to collect and dilute a biological sample.

FIG. 1B is a cross-sectional top-down view of the device of FIG. 1A, corresponding to a view 1B in FIG. 1A.

FIG. 8A is cut-away side-view of another device to collect and dilute a biological sample.

FIG. 8B is a cut-away side-view of a cap to seal a fluid outlet of the device of FIG. 8A.

Figure 2A:
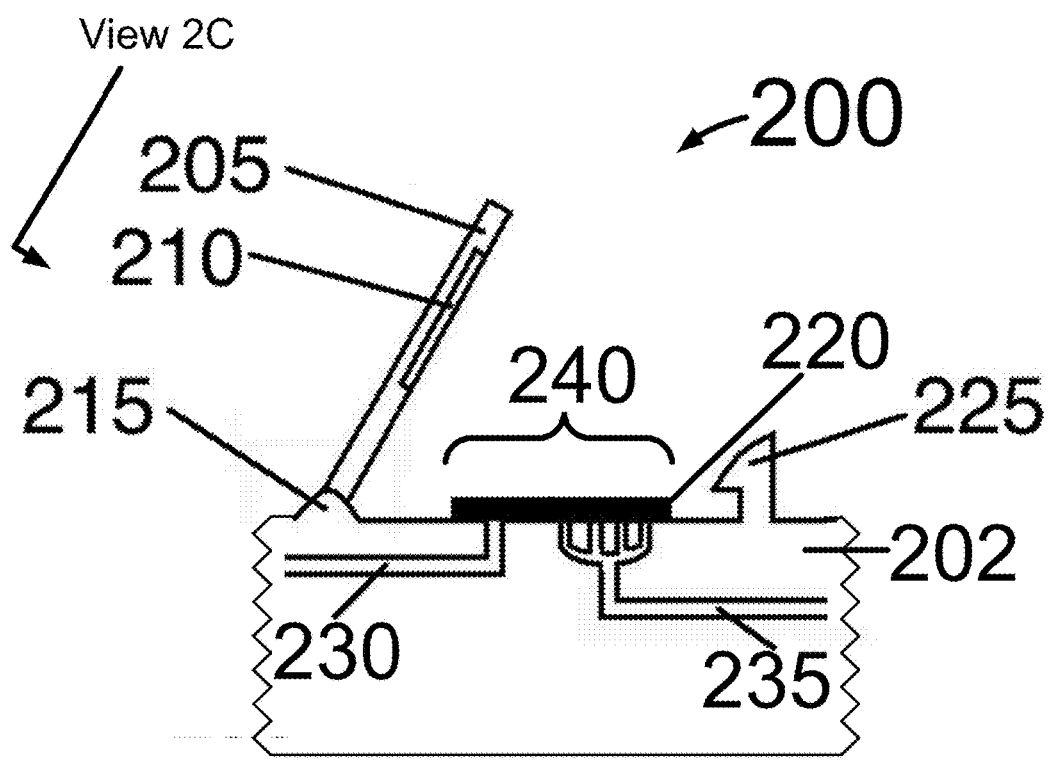
FIG. 2A is cut-away side-view of a portion of another device to collect and dilute a biological sample.

In the drawings, the leftmost digit(s) of a reference number may identify the drawing in which the reference number first appears.

DETAILED DESCRIPTION

FIG. 1A is a cut-away side-view of a sample processing device 100 to collect and dilute a biological sample.

FIG. 1B is a cross-sectional top-down view of device 100, corresponding to a view 1B in FIG. 1A.

Device 100 includes a housing 102 having an inlet 150 and a first chamber 120, also referred to herein as a sample chamber 120, to collect or receive a biological sample through inlet 150. Device 100 may be configured to collect or receive a predetermined volume of the biological sample in sample chamber 120.

Device 100 further includes a reagent chamber 125, which may be pre-loaded with a reagent.

Device 100 further includes a first plunger 110 structured to slide into sample chamber 120, and a second plunger 115 structured to slide into reagent chamber 125. Device 100 further includes an external mechanical actuator 105 to control first and second plungers 110 and 115.

External actuator 105 may be configured to simultaneously move plungers 110 and 115, to cause plunger 110 to move the biological sample from sample chamber 120 through a fluid outlet of chamber 120, and to cause plunger 115 to move the reagent from reagent chamber 125 through a fluid outlet of chamber 125.

Device 100 may be configured to combine and/or mix the biological sample and reagent in a mixing chamber 130, and to dispense the combined biological sample and reagent through a fluid path 132 to a fluid outlet 134.

Fluid outlet 134 may correspond to a fluid outlet of device 100, and may be configured to receive an attachment, such to provide the combined biological sample and reagent to one or more other devices and/or tools, such as for processing and/or diagnostics. The one or more other devices and/or tools may include, without limitation, a cassette and/or lateral flow strip.

Alternatively, or additionally, housing 102 may include an assay region to receive fluid from fluid path 132 and/or fluid outlet 134. The assay region may include, without limitation, a lateral flow strip.

Device 100 may be configured to seal sample chamber 120 upon activation of external actuator 105. Device 100 may include, for example, an exterior cover to seal inlet 150 and prevent the sample from exiting device 100 through inlet 150 upon activation external actuator 105, such as described below with reference to FIG. 2D.

Device 100 may be configured to combine and/or mix the biological sample from sample chamber 120 with a predetermined volume of liquid reagent from reagent chamber 125 in mixing chamber 130. Device 100 may be further configured to combine and/or mix the biological sample and the liquid reagent from reagent in accordance with a predetermined ratio. In FIG. 1B, for example, cross-sectional areas of sample chamber 120 and reagent chamber 125 sized or dimensioned to provide a desired reagent to sample ratio.

In some embodiments sample chamber 120 and reagent chamber 125 are positioned in series with respect to each other.

Device 100 may further include a filter, which may be positioned within a filter area proximate to sample inlet 150. In the examples of FIGS. 1A and 1B, device 100 includes a filter 145.

Filter 145 may be structured or configured to filter or remove unwanted material from a collected sample such as, for example, to remove red or white blood cells from a blood sample. A red blood filter may be useful to provide blood plasma to sample chamber 120 through inlet 150. Filter 145 may include a pad made from a material selected from the following: nitrocellulose, glass fiber, nylon, and/or other synthetic(s) material and/or compound. Filter 145 may include one or more reagents thereon and/or therein, (e.g., dried on filter 145), to contact and/or treat the biological sample.

Device 100 may include a wick within inlet 150, which may be in contact with filter 145 to draw liquid through filter 145 into sample chamber 120.

Device 100 may include a capillary tube between filter 145 and sample chamber 120 to collect a predetermined volume of a filtered biological sample from filter 145. Device 100 may be may be configured to fill the capillary tube and retain any excess biological sample in the filter area.

FIG. 2A is cut-away side-view of a portion of a device 200 to collect and dilute a biological sample. FIGS. 2B through 2F illustrate example features of device 200. One or more features described below with reference to FIGS. 2A through 2F may be combined with one or more features described above with respect to device 100. Device 100 is not, however, limited to the examples of FIGS. 2A through 2F.

In FIG. 2A, device 200 includes a housing 202 having a sample receiving region 240, a fluid inlet 230 to sample receiving region 240, and a fluid outlet 235 from sample receiving region 240. Fluid inlet 230 may be configured to provide a reagent from a reagent chamber and/or a wash solution to sample receiving region 240.

Sample receiving region 240 may include a sample well.

Device 200 further includes a door or cover 205 to enclose sample receiving region 240. Door 205, when closed, may form one or more chambers within and/or adjacent to sample receiving region 240. Cover 205 may have a fluid path 210 to provide fluid from fluid inlet 230 to sample receiving region 240 when in a closed position. Fluid path 210 may be configured to distribute the fluid over an area of sample receiving region 240.

Figure 2B:
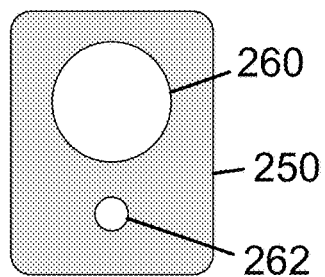
FIG. 2B illustrates example features of the device of FIG. 2A.
Figure 2C:
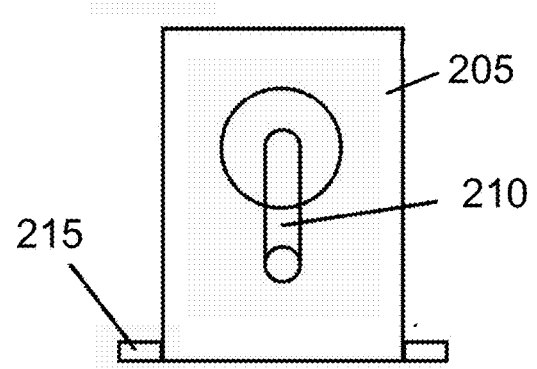
FIG. 2C illustrates example features of the device of FIG. 2A.

In the example of FIG. 2A, device 200 further includes a hinge 215 to hingedly connect cover 205 to housing 202. Also in the example of FIG. 2A, housing 202 includes a latch 225 to retain cover 205 when cover 205 is placed in the closed position. FIG. 2C is a top-down view of device 200 corresponding to a view 2C in FIG. 2A, illustrating door 205, fluid path 210, and hinge 215. Device 200 is not, however, limited to a hinged cover.

Figure 2D:
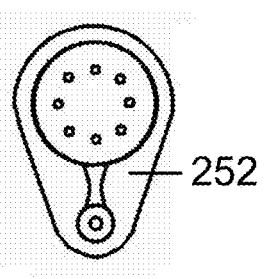
FIG. 2D illustrates example features of the device of FIG. 2A.
Figure 2E:
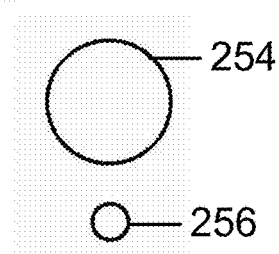
FIG. 2E illustrates example features of the device of FIG. 2A.
Figure 2F:
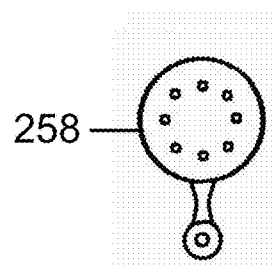
FIG. 2F illustrates example features of the device of FIG. 2A.

Housing 202 may have a sealing surface 220 to seal sample receiving region 240 when cover 205 is in the closed position. Sealing surface 220 may include a gasket 250 in FIG. 2B, a deformable surface 252 in FIG. 2D, O-rings 254 and 256 in FIG. 2E, and/or a deformable surface 258 in FIG. 2F. In FIG. 2B, gasket 250 has an opening 260 corresponding to sample receiving region 240 in FIG. 2A, and an opening 262 corresponding to fluid path 210 in FIG. 2A. Similar openings are illustrated in FIGS. 2D, 2E, and 2F.

Figure 3A:
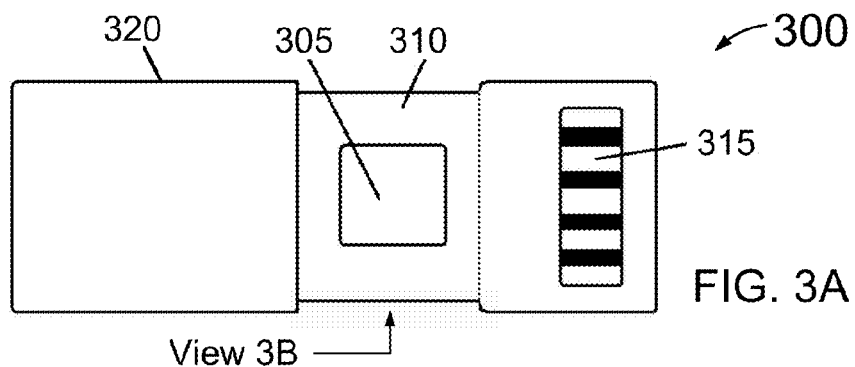
FIG. 3A is top-down view of another device to collect, dilute, and test a biological sample.

FIG. 3A is top-down view of a device 300 to collect, dilute, and test a biological sample. Device 300 includes a housing having a sample inlet 305, a sealing surface 310, a sliding surface 320, and a lateral flow test 315. Sealing surface 310 and sliding surface 320 may be configured to slide toward one-another to seal sample inlet 305 and/or to activate device 300, such as described in one or more examples below.

Figure 3B:
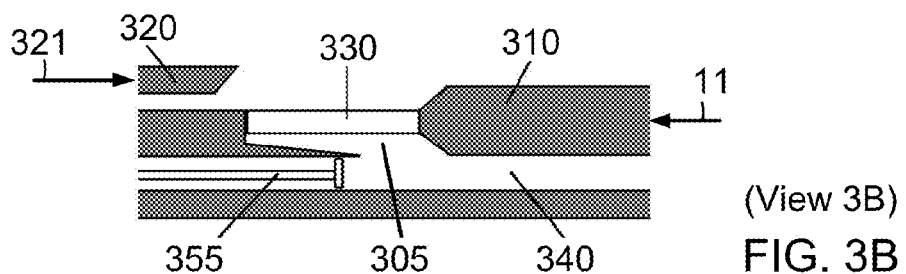
FIG. 3B is a cut-away side-view of a portion of the device of FIG. 3A.

FIG. 3B is a cut-away side-view of device 300, corresponding to a view 3B in FIG. 3A, in which sealing surface 310 and sliding surface 320 are configured to slide toward one-another in the directions of corresponding arrows 311 and 321, to seal sample collection area 305 and to activate or control a sample plunger 335 to move a sample from sample inlet 305 into and/or through a sample chamber 340.

In the example of FIG. 3B, device 300 further includes a sample collection pad 330 within sample inlet 305.

Figure 3C:
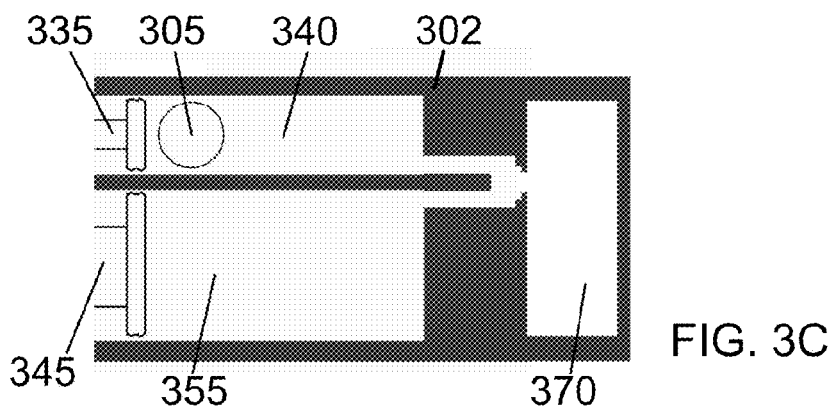
FIG. 3C is a cut-away top-down view of a portion of the device of FIG. 3A.

FIG. 3C is a cut-away top-down view of a portion of device 300, including sample inlet 305, sample plunger 335, and sample chamber 340 within a housing 302. Housing 302 further includes a reagent chamber 350 and a reagent plunger 345. Sample plunger 335 and reagent plunger 345 may be mechanically linked to the closing of device 300, and may be configured to activate when sealing surface 310 and sliding surface 320 (FIGS. 3A and 3B) are pressed together to seal sample inlet 305.

Plungers 335 and 345 may be configured to move contents of sample chamber 340 and reagent chamber 355, respectively, such as described in one or more examples herein. In the example of FIG. 3C, housing 302 further includes a collection chamber 370 to receive, combine, and/or mix contents of sample chamber 340 with contents of chamber 355.

Figure 3D:
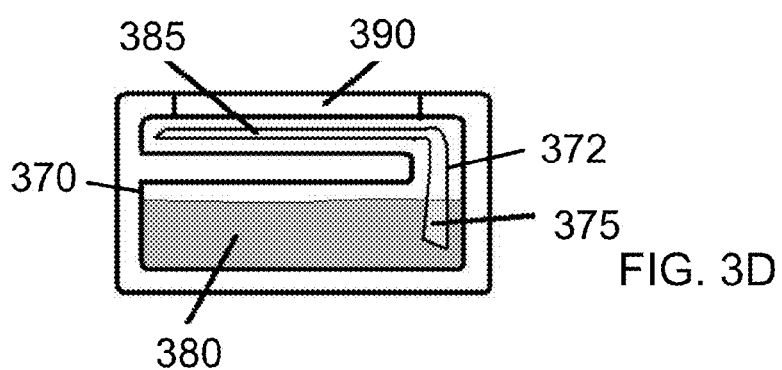
FIG. 3D is a cross-sectional view of a portion of the device of FIG. 3A.

FIG. 3D is a cross-sectional view of device 300 (side-view or end-view), in which collection chamber 370 is illustrated with a mixture 380 of a liquid reagent and sample. In the example of FIG. 3D, housing 302 further includes a fluid passage 372 between collection chamber 370 and a test region 385, and a wicking material 375 within fluid passage 372 to wick mixture 380 to test region 385. Lateral flow test 315 (FIG. 3A) may be positioned within test region 385 to permit viewing of test results through a window 390.

Figure 4A:
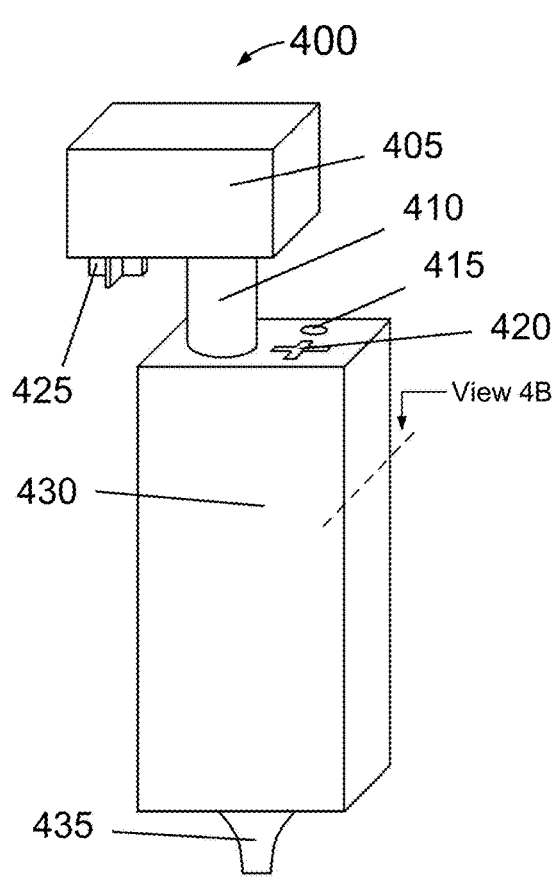
FIG. 4A is a perspective view of another sample processing device to collect and dilute a biological sample.
Figure 4B:
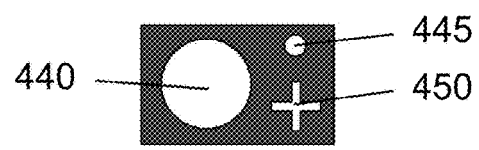
FIG. 4B illustrates example features of the device of FIG. 4A.
Figure 4C:
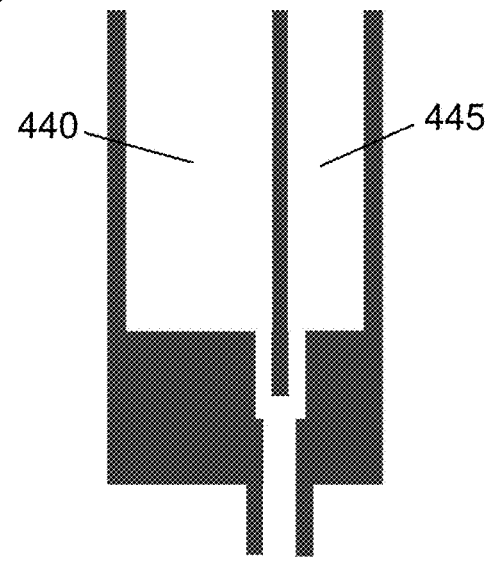
FIG. 4C illustrates example features of the device of FIG. 4A.

FIG. 4A is a perspective view of a sample processing device 400 to collect and dilute a biological sample. FIGS. 4B and 4C illustrate example features of device 400.

Device 400 includes a top portion 405 having an alignment key 425 extending therefrom, body portion 430 having a key slot 420 to receive key 425, a sample port 415 to receive a sample, a rotatable plunger 410, and a nozzle 435.

Top portion 405 is rotatable about plunger 410 to align key 425 with slot 420. When key 425 is aligned with slot 420, top portion 405 may be pressed towards body portion 430 to activate plunger 410.

When key 425 is aligned with slot 420, sample inlet 415 may be aligned with a sealing surface, tube, and/or plunger within body portion 405 to provide a sealed chamber.

FIG. 4B is top-down cross-sectional view of body portion 430, corresponding to view 4B in FIG. 4A. In FIG. 4B, body portion 430 has a liquid reagent chamber 440 dimensioned to accommodate plunger 410, a sample chamber 445, and an opening 450 dimensioned to accommodate key 425.

FIG. 4C is a cut-away side-view of body portion 430, depicting liquid reagent chamber 440 and sample chamber 445.

Figure 5:
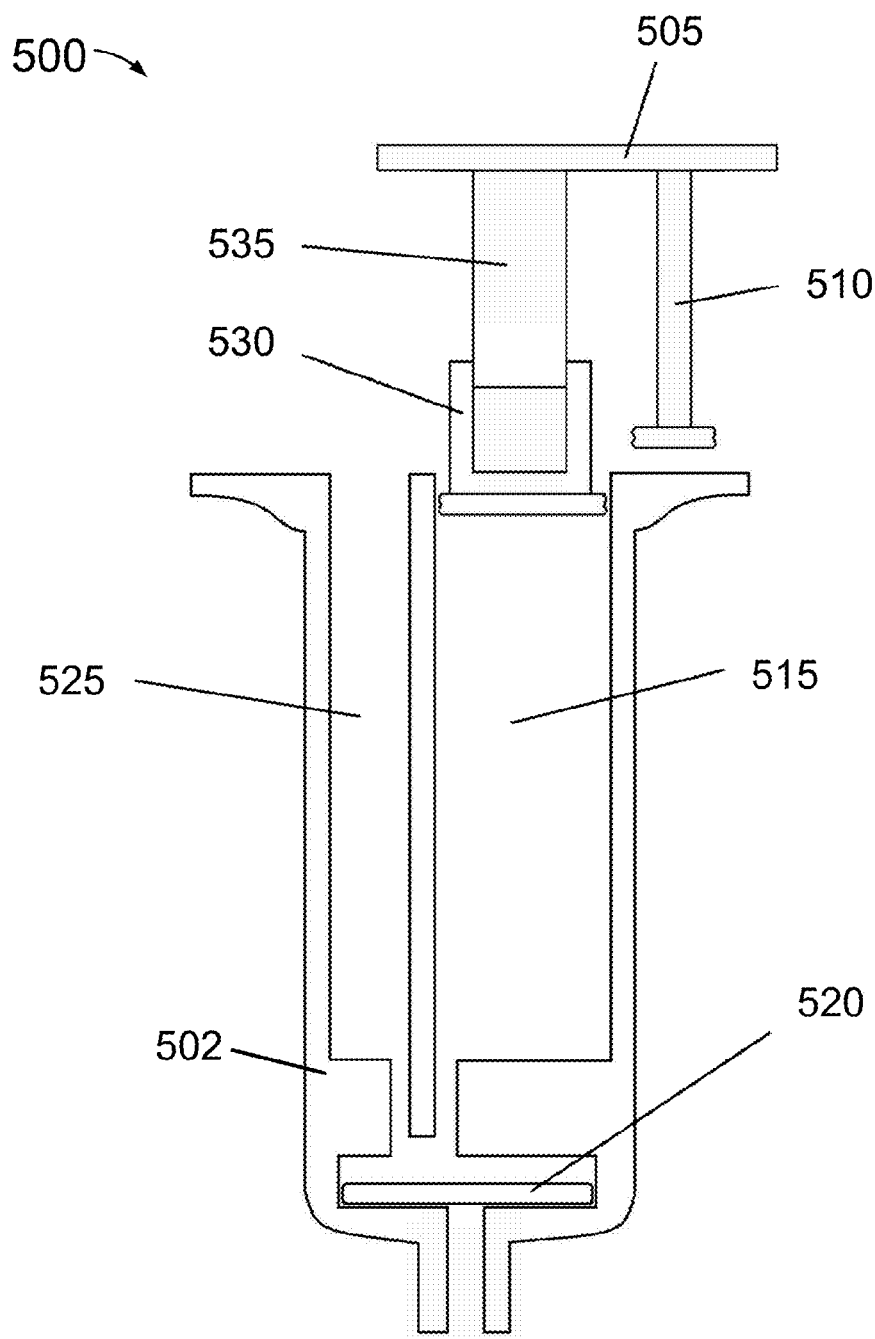
FIG. 5 is a cut-away side-view of another sample processing device to collect and dilute a biological sample.

FIG. 5 is a cut-away side-view of a sample processing device 500 to collect and dilute a biological sample. Device 500 includes a housing 502 having a liquid reagent chamber 515 and a sample chamber 525, illustrated herein in a parallel configuration. Device 500 further includes a filter 520 downstream of parallel chambers 525 and 515. Device 500 further includes a first plunger, including a nested plunger upper portion 535 and a nested plunger lower portion 530 in liquid reagent chamber 515. Device 500 further includes a second plunger 510 that is rotatable into sample chamber 525, such as after addition of a sample. Nested plunger portions 535 and 530, and plunger 510 are mechanically linked by an actuator portion 505.

Figure 6:
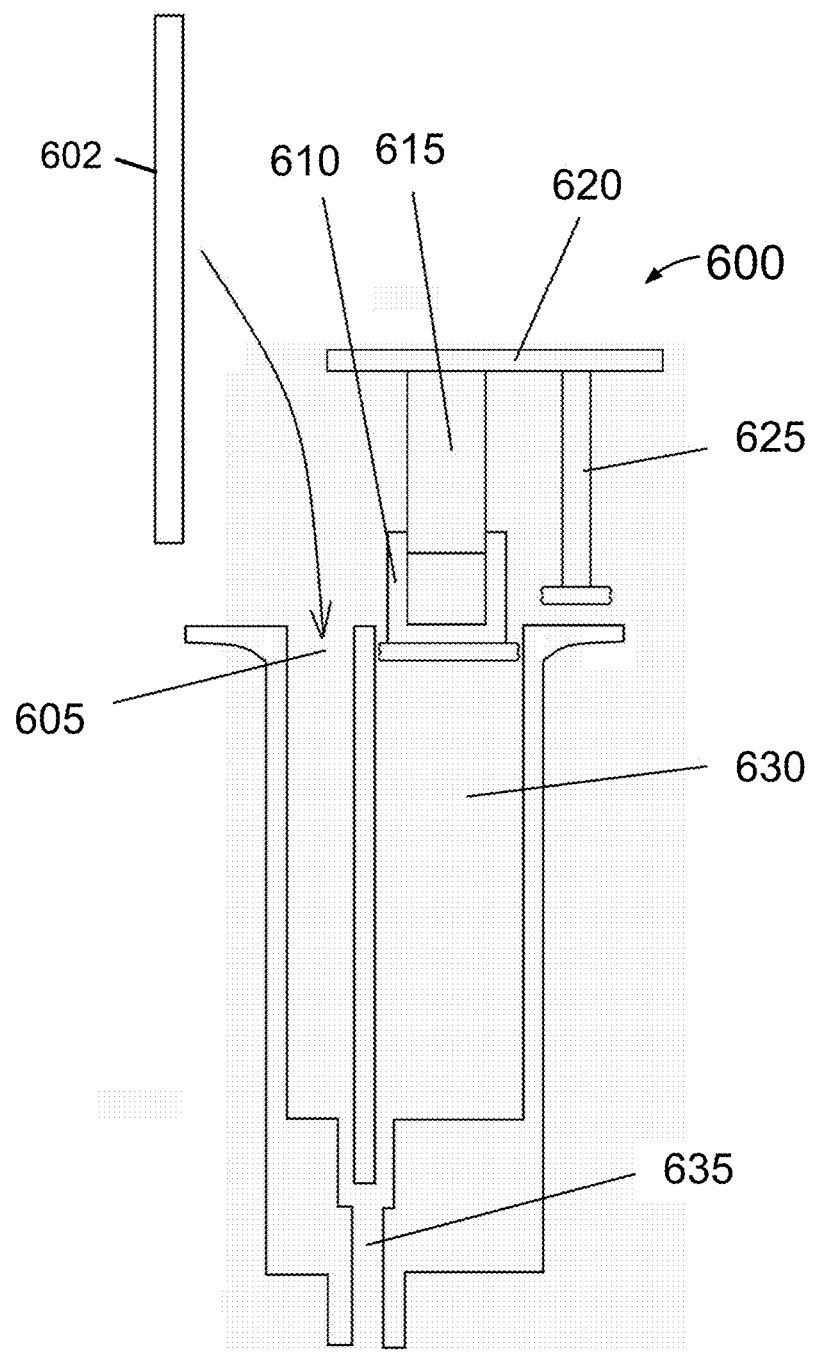
FIG. 6 is a cut-away side view of a sample processing device having a capillary tube port to receive a capillary tube.

FIG. 6 is a cut-away side view of a sample processing device 600 having a capillary tube port 605 to receive a capillary tube 602. Capillary tube 602 may be configured to collect or receive a sample for transfer to device 600.

Device 600 includes a sample plunger 625, a liquid reagent plunger 610 and a corresponding nested plunger 615 dimensioned for a liquid reagent chamber 630. Device 600 further includes a mechanical actuator 620 to link liquid reagent plunger 615 to sample plunger 625.

Mechanical actuator 620 is twistable to align plunger 625 with capillary port 605. When plunger 625 is aligned with capillary port 605, actuator 620 is depressible to dispense sample from capillary tube 602 and liquid reagent from liquid reagent chamber 630, and through a fluid outlet 635 where the sample and the liquid reagent mix. The sample may be dispensed from capillary tube 602 by plunger 625, alone and/or in combination with air pressure and/or additional liquid.

Figure 7A:
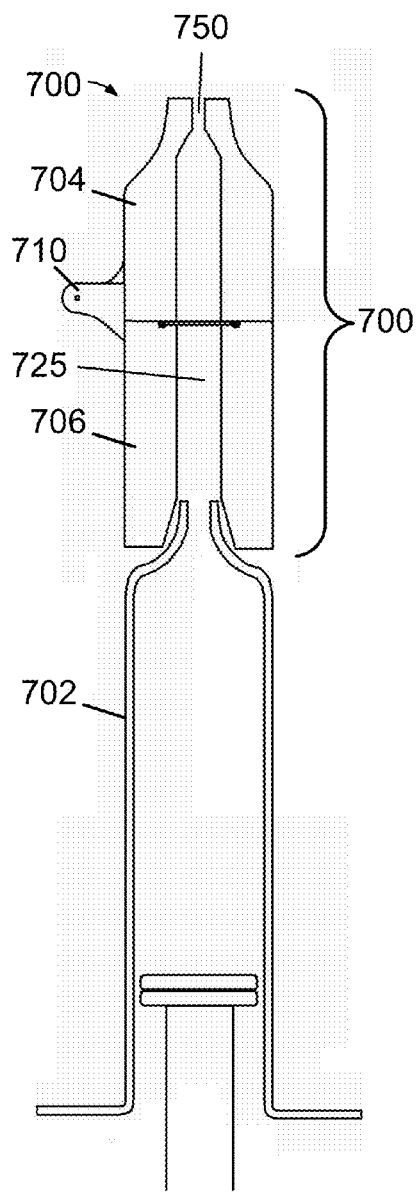
FIG. 7A is a cut-away side-view of a sample processing device to receive a syringe.

FIG. 7A is a cut-away side-view of a sample processing device 700 to receive a syringe 702. Device 700 includes first and second housing portions 704 and 706, respectively, hingedly connected to one another with a hinge 710. In the example of FIG. 7A, device 700 is illustrated in a closed position.

Figure 7B:
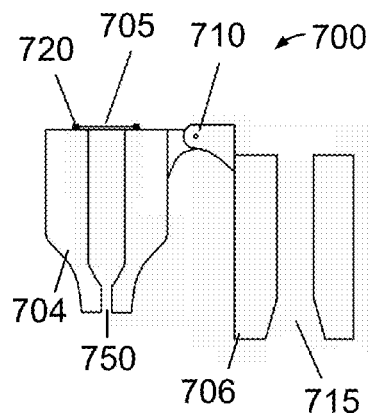
FIG. 7B is a cut-away side-view of the device of FIG. 7A in an open position.

FIG. 7B is a cut-away side-view of device 700 in an open position.

Figure 7C:
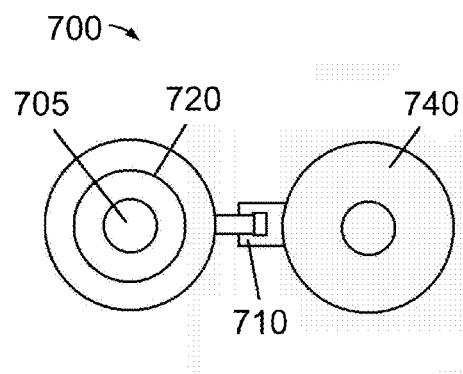
FIG. 7C is a top-down view of the device of FIG. 7A in the open position.

FIG. 7C is a top-down view of device 700 in the open position.

Device 700 includes first and second housing portions 704 and 706, respectively. Device 700 further includes a sample collection area 705 and a syringe inlet 715 to receive syringe 702.

In the open position, sample collection area 705 is exposed to receive a sample.

In the closed position, a sealing surface 720 first housing portion 704 contacts a surface 740 of second housing portion 706 to enclose sample collection area 705, and device 700 provides a fluid path 725 between syringe inlet 715 and a fluid outlet 750, through sample collection area 705.

To operate, sample is added to sample area 705 while device 700 is in the open position. Device 700 may then be closed latched to enclose and seal sample collection area 705. When syringe is inserted at syringe inlet 715, a liquid within syringe 715 may dispensed through fluid path 725 and a corresponding product may be collected at fluid outlet 750.

FIG. 8A is cut-away side-view of a device 800 to collect and dilute a biological sample.

Device 800 includes an outer housing portion 870, and an inner housing portion 868 having a sample chamber 835 and liquid reagent chamber 840.

Device 800 is configured to mix sample from chamber 835 and liquid reagent from chamber 840 at a fluid outlet 845.

There is a sample inlet 850 and a sample filter 855.

Device 800 may include a sample filter 855, such as described in one or more examples herein.

Device 800 may include one or more nested or multistage plungers to initiate multiple mechanical actions. In the example of FIG. 8, a sample plunger includes a plunger portion 805 to nest within a plunger portion 810, to nest within a plunger portion 815. Also in FIG. 8, a liquid reagent plunger includes a plunger portion 820 to nest within a plunger portion 825, to nest within a plunger portion 830.

Device 800 further includes a mechanical actuator 860 to link the sample and reagent plungers to dispense sample and reagent proportionally. In FIG. 8, mechanical actuator 860 is configured to move internal housing portion 865 relative to outer housing portion 870, to close or seal sample inlet 850 against an inner wall of outer housing portion 870, and provide a sealed chamber.

Plunger portion 815 may include a retractable arm 802 to prevent plunger portion 815 from inserting further into sample chamber 835 until housing portions 865 and 870 are positioned to seal sample inlet 850 as described. Similarly, plunger portion 830 may include a retractable arm 804 to prevent plunger portion 830 from inserting further into reagent chamber 840 until sample inlet 850 is sealed.

Device 800 may include a plunger 875 to clear liquid from fluid outlet 845 after sample chamber 835 and reagent chamber 840 are emptied. This may permit greater volume output from each run.

In some embodiments a length of sample collection chamber 835 is positioned next to a length of reagent chamber 840. Where the lengths are the same, the sample and reagent solutions may dispense at a proportional rate to provide a solution that is evenly mixed as it is dispensed.

In some embodiments either sample chamber 835 and/or reagent chamber 840 may have multiple stages to release first one fluid and then another fluid.

In some embodiments one or more plungers is mechanically linked to one or more covers. In such an embodiment, activation of the plunger(s) also moves the corresponding cover(s) into place to close or seal sample collection area 885 to prevent contamination or leaking.

Device 800 may include a cover or cap to plug or seal a fluid output 845 prior to use, such as described below with reference to FIG. 8B.

FIG. 8B is a cut-away side-view of a cap 882, including a plug 884 to seal fluid outlet 845 of device 800 in FIG. 8A, and a cavity or well 886 to receive a wall 880 extending from outer housing portion 870 of device 800. Cap 882 is not necessarily illustrated in proportion to features of device 800 in FIG. 8A.

Plug 884, or a portion thereof may be configured to insert snugly within fluid outlet 845 in FIG. 8A, and/or to seal against a surface inner housing 865 in FIG. 8A. A portion of plug 884 may be configured to insert snugly within an opening 881 of outer housing portion 870 in FIG. 8. Cap 882 may be used plug fluid outlet 845 prior to running or activating device 800, and may be removed before use or activation of device 800. Cap 882 may be configured to prevent accidental activation of device 800.

Examples are provided herein in which a device is configured to dispense fluids from a sample chamber and a reagent chamber in parallel with one another. Methods and systems disclosed herein are not, however, limited to parallel arrangements and, unless specified otherwise herein, such devices may be configured to dispense fluids from a sample chamber and a reagent chamber serially.

A device as described in one or more examples above may include one or more features described below with respect to FIGS. 9A through 9D. The examples above are not, however, limited to the examples of FIGS. 9A through 9D.

FIGS. 9A through 9D illustrate a sample processing device 900 to collect, measure, and dispense a biological sample 904 (illustrated herein with shading).

Device 900 includes a housing that has a sample collection well 902 therein to receive a biological sample 904, and a sample chamber 906 to having an opening at a first end to receive biological sample 904 from well 902.

Sample chamber 906 may be dimensioned (e.g., with a sufficiently small cross-sectional diameter), such that surface tension caused by cohesion within biological sample 904, and/or adhesive forces between biological sample 904 and a wall or surface of sample chamber 906, act to draw biological sample 904 from well 902. Such action may be referred to herein as capillary action, and sample chamber 906 may be referred to herein as a capillary tube.

Device 900 may include a valve, such as a surface tension valve, at second end of capillary tube 906 to retain biological sample 904 within capillary tube 906.

The housing may include an opening through a surface thereof to provide biological sample 904 to well 902. Device 900 may include a permeable material positioned within the opening, such as a membrane or pad. The permeable surface may include a marking to indicate a point or position at which to apply biological sample 904. The marking may include, for example, a circular marking having an outer ring of a first color (e.g., red), and an inner circle of a second color (e.g., white), such as to indicate a position at which to place a pinpricked finger to collect a blood sample. The marking, or a portion thereof, may be placed on a surface of the housing around the opening to well 902.

Device 900 may be configured and/or calibrated to receive, capture, and/or hold a predetermined amount of biological sample 904, and may include a marking 910 to indicate a position along capillary tube 920 that corresponds to the pre-determined amount of biological sample 905. In an embodiment, capillary tube 906, alone and/or in combination with well 902, is configured and/or calibrated to receive, capture, and/or hold the predetermined amount of biological sample 904, and marking 910 positioned at an end of capillary tube 906, opposite well 902, to identify a point at which capillary tube 906 is full.

Device 900 may be configured or implemented such that marking 910 and biological sample 904 within capillary tube 906, or within at least a portion of capillary tube 906 proximate to marking 910, is visible to a user. For example, capillary tube 906, or a portion thereof, may be optically transparent and may be exposed to a user, along with marking 910, at least during a sample collection phase.

Figure 9A:
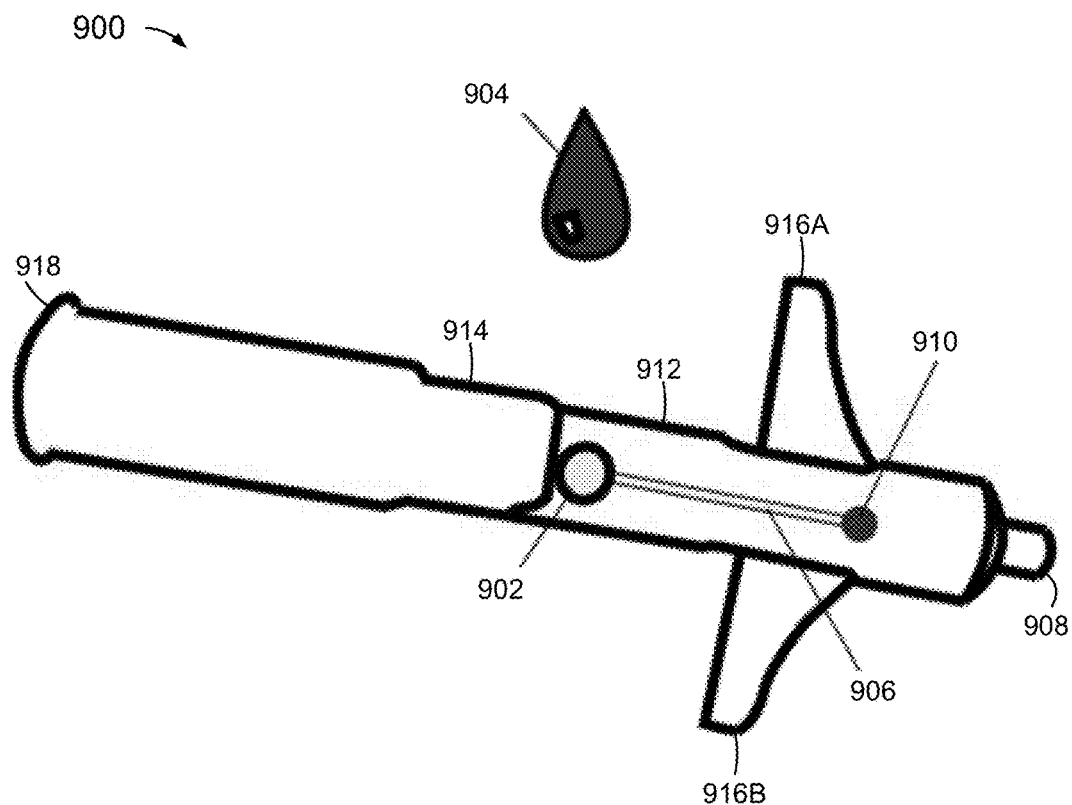
FIG. 9A is a side view of a sample collection device.

FIG. 9A illustrates device 900 prior to introduction of biological sample 904.

Figure 9B:
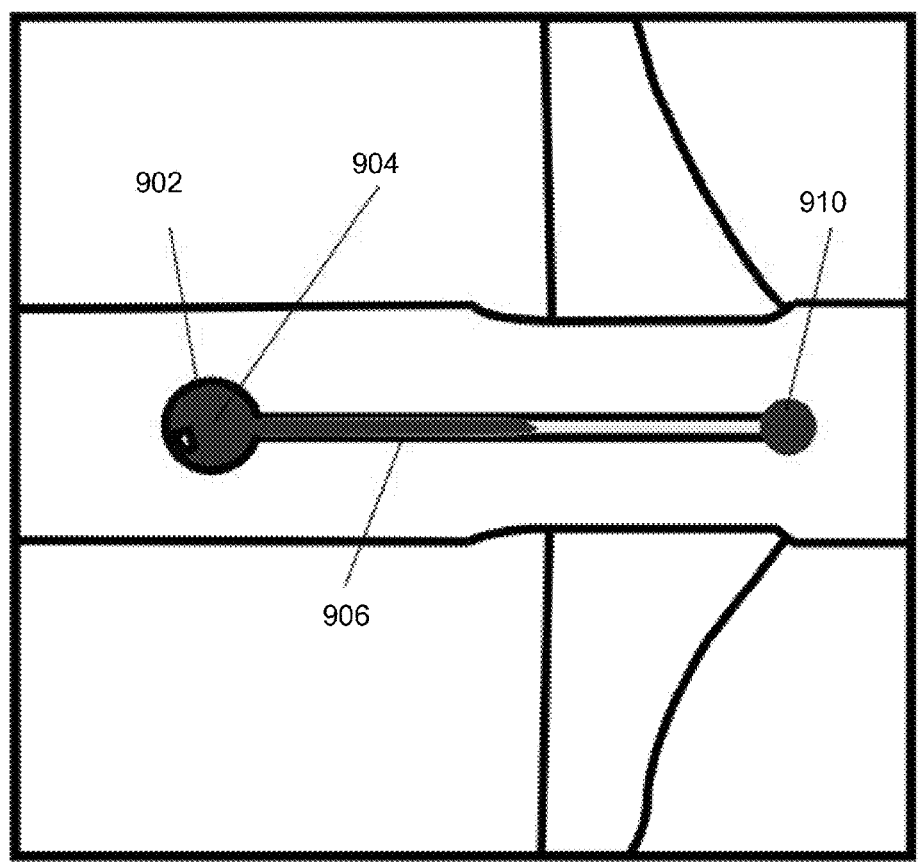
FIG. 9B is a view of the sample collection device viewed from exterior of the collection device.

In FIG. 9B, collection well 902 and a portion of capillary tube 906 include a biological sample 904. Indicator 910 provides a visual indication that insufficient biological sample 904 has been collected. In this situation, a user may need to wait for until capillary tube 906 to fill with biological sample 904. If biological sample 904 is not advancing within capillary tube 906, the user may need to add or provide additional biological sample 904.

Figure 9C:
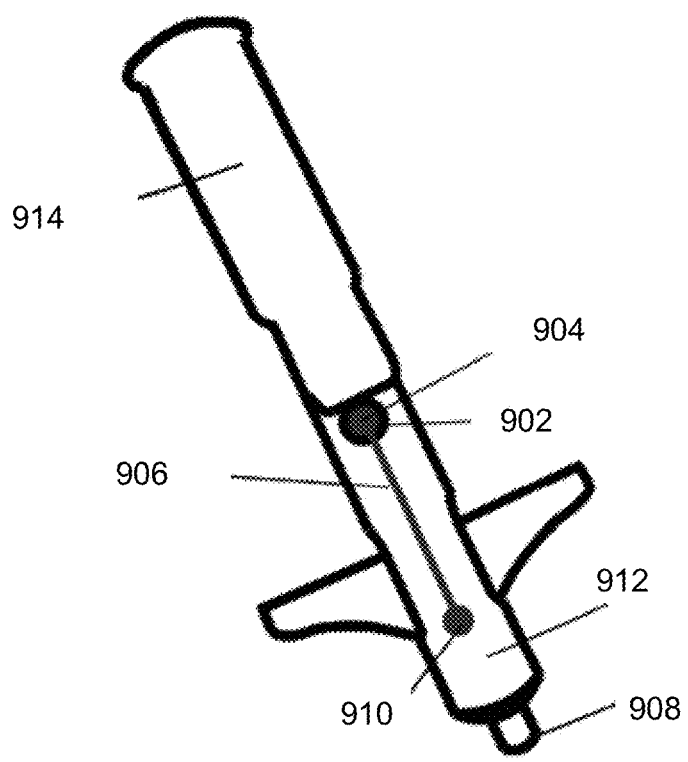
FIG. 9C is a side view of the collection device with a sample collection and measuring feature filled with biological sample.

In FIG. 9C, capillary tube 906 is filled with biological sample 904, up to marking 910, indicating that device 900 contains sufficient (i.e., the pre-determined amount of) biological sample 904. In the example of FIG. 9C, the shading of biological sample 904 effectively "connects the dots" of well 902 and indicator 910.

The housing of device 900 may include first and second portions 912 and 914, respectively. First portion 912 may be referred to herein as a cap. First portion 912 may be extendable from within a second portion 912, in a telescoping fashion, to place device 900 in a first position in which the opening to well 902 is exposed to a user. The first position may also be referred to herein as an open position and/or a sample collection position. FIGS. 9A and 9C illustrate device 900 in the sample collection position.

Figure 9D:
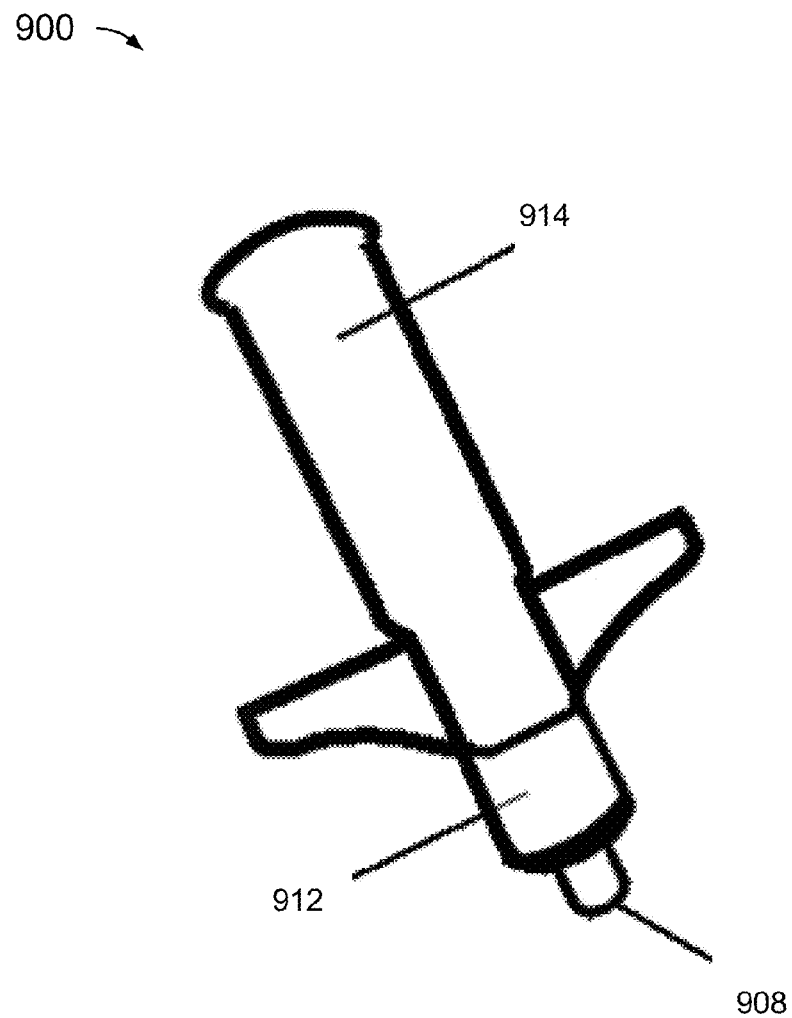
FIG. 9D is a side view of the sample collection device after being activation.

After biological sample 904 is received or collected within capillary tube 906, first and second portions 912 and 914 may be pressed towards one another to place device 900 in a second position in which the opening to well 902 is sealed, such as illustrated in FIG. 9D. The second position may also be referred to herein as a closed collection position.

Device 900 may be configured such that marking 910 and at least a portion of capillary tube 906 are exposed or visible to a user when in the open position, such as described further above. Device 900 may be further configured such marking 910 and capillary tube 906 are concealed by cap 914 when in the closed position. Alternatively, marking 910 and capillary tube 906, or a portion thereof, may remain exposed when device 900 is in the closed position.

Device 900 may be further configured such that collection well 902 and/or a marking proximate to the opening to well 902, are exposed or visible exterior of device 900 when in the open position and/or in the closed position.

In an embodiment, device 900 is configured such that collection well 902, marking 910, and a portion of capillary tube 906 proximate to marking 910 are exposed when in at least the first position, and a remaining portion of capillary tube 906 is concealed in the first position and the second position.

The housing of device 900 may include one or more extensions 916, which may serve as a finger grasp. For example, an end 918 of device may be positioned within a palm of a hand, and extension(s) 916 may be grasped with fingers of the hand to compress first and second portions 912 and 914 toward one another.

Device 900 may further include a fluid controller and mechanical actuator to dispense biological sample 904 from capillary tube 906. The mechanical actuator may be configured to actuate the fluid controller as device 900 is moved from the open position to the closed position. In this example, closing of device 900 may be referred to as activating or running device 900.

During activation, plungers within the cap 914 may be controllable to dispense biological sample 904 from capillary tube 906. Device may be configured such that biological sample 904 is dispensed directly from capillary tube 906 through an outlet or nozzle 908. In another embodiment, the housing of device 900 includes a reagent chamber to hold a liquid reagent, and one or more plunger are configured to dispense and mix biological sample 904 proportionally with the liquid reagent, internal of the housing.

Device 900 may be configured to dispense the mixture of biological sample 904 and liquid reagent as they are mixed, and/or may be configured to hold the mixture for a period of time, such as for a pre-determined assay period, and/or for storage and/or transport.

Nozzle 908 may be configured to mate with a fluid inlet of an assay device and/or sample holding or transport device.

Device 900 may be configured and/or implemented as part of an assay device.

In an embodiment a length of a capillary tube extends alongside a length of a reagent chamber, and a fluid controller is configured to dispense and mix biological sample from the capillarity tube and reagent from the reagent chamber in parallel with one another. In an example, the length of the capillary tube is the same as the length of the reagent chamber, and a volume of the capillary tube differs from a volume of the reagent chamber to provide a pre-determined proportional mixture. In another example, the length of the capillary tube is the same as the length of the reagent chamber and the volume of the capillary tube is the same as the volume of the reagent chamber to provide a mixture of equal proportions of biological sample and reagent.

In another embodiment, the fluid controller is configured to dispense biological sample from the capillarity tube and reagent from the reagent chamber serially with respect to one another.

In an embodiment a capillary tube and/or a reagent chamber include multiple stages, and a fluid controller is configured to serially dispense the stages.

Methods and systems are disclosed herein with the aid of functional building blocks illustrating the functions, features, and relationships thereof. At least some of the boundaries of these functional building blocks have been arbitrarily defined herein for the convenience of the description. Alternate boundaries may be defined so long as the specified functions and relationships thereof are appropriately performed.

While various embodiments are disclosed herein, it should be understood that they have been presented by way of example only, and not limitation. It will be apparent to persons skilled in the relevant art that various changes in form and detail may be made therein without departing from the spirit and scope of the methods and systems disclosed herein. Thus, the breadth and scope of the claims should not be limited by any of the example embodiments disclosed herein.

What is claimed is:

1. An apparatus, comprising:
   a portable housing having a cavity therein to receive a biological sample through an opening through a surface of the housing, a sample chamber, a first opening of the sample chamber through which to draw the biological sample from the cavity through capillary action, and a second opening of the sample chamber through which to dispense the biological sample; and
   a first indicator calibrated with respect to the sample chamber;
   wherein at least a portion of a wall of the sample chamber adjacent to the first indicator is optically transparent and visible exterior of the housing;
   the housing is mechanically configurable in a first configuration to receive the biological sample, and mechanically re-configurable from the first configuration to a second configuration;
   the housing is configured to close the cavity when the housing is re-configured from the first configuration to the second configuration; and
   a mechanically actuated fluid controller to dispense fluid from the sample chamber through the second opening of the sample chamber, as the housing is mechanically reconfigured from the first configuration to the second configuration.

2. The apparatus of claim 1, wherein the first indicator includes one or more markings calibrated with respect to one or more of:
   a position along a length of the sample chamber that corresponds to a pre-determined volume of the biological sample; and
   a position along a length of the sample chamber that corresponds to completion of receipt of the biological sample.

3. The apparatus of claim 1, wherein:
   the housing further includes reagent region to hold a reagent, a fluid outlet, and one or more fluid paths amongst the second opening of the sample chamber, the reagent region, and the fluid outlet; and
   the mechanically actuated fluid controller is further to dispense fluid from the reagent region to the fluid outlet.

4. The apparatus of claim 3, wherein the housing and the mechanically actuated fluid controller are configured to dispense the biological sample and the reagent based on a pre-determined ratio.

5. An apparatus, comprising:
   a portable housing having a cavity therein to receive a biological sample through an opening through a surface of the housing, a sample chamber, a first opening of the sample chamber through which to draw the biological sample from the cavity through capillary action, and a second opening of the sample chamber through which to dispense the biological sample;
   a first indicator calibrated with respect to the sample chamber;
   wherein at least a portion of a wall of the sample chamber adjacent to the first indicator is optically transparent and visible exterior of the housing;
   the housing further includes a reagent region to hold a reagent, a fluid outlet, and one or more fluid paths amongst the second opening of the sample chamber, the reagent region, and the fluid outlet;
   a mechanically actuated fluid controller to dispense fluid from the second opening of the sample chamber and from the reagent region to the fluid outlet; and
   wherein the reagent region includes multiple reagent chambers, and wherein the housing and the mechanically actuated fluid controller are configured to dispense reagent from the multiple reagent chambers to successive stages of actuation of the mechanically actuated fluid controller through successive fluid paths.

6. The apparatus of claim 5, wherein the mechanically actuated fluid controller is further configured to dispense the biological sample and a portion of the reagent in accordance with a pre-determined ratio.

7. The apparatus of claim 5, wherein the fluid controller includes at least one of:
   multiple fluid controllers mechanically linked to one another;
   multiple controllers of different sizes mechanically linked to one another;
   multiple nested portions to provide staged actions as the fluid controller is moved from a first position to a second position; and
   multiple nested portions to provide staged actions as the fluid controller is moved from a first position to a second position, and a portion to activate another fluid controller to clear remaining liquid from the fluid outlet.

8. The apparatus of claim 5, further including at least one of:

a mechanically-releasable lock to preclude actuation of the fluid controller when engaged; and a rotatable mechanical actuator to unlock the fluid controller when rotated into a predetermined position.

9. The apparatus of claim 5, wherein the housing further includes an assay region adjacent to the fluid outlet.

10. The apparatus of claim 5, wherein the housing further has a mixing region within a fluid path to the fluid outlet to mix the biological sample and the reagent.

11. The apparatus of claim 5, wherein the sample chamber includes multiple chambers to receive the biological sample.

12. The apparatus of claim 5, further including a filter positioned within the first opening of the sample chamber.

13. The apparatus of claim 5, wherein the housing has a well to retain excess biological sample to prevent overfilling of the sample chamber.

14. A device for collecting a biological sample comprising:

a housing having a sample collection well formed therein to receive a biological sample;

a capillary tube disposed within the housing, the capillary tube having an opening at a first end to receive the biological sample from the well, and the capillary tube dimensioned with a cross-sectional diameter such that capillary action draws the biological sample from the well into the capillary tube;

the housing further including first and second portions, with the first portion extendable from the second portion to place the device in a first position thereby providing an opening to the well, and the first and second portions configured to be pressed towards one another to place the device in a second position in which the opening to the well is sealed; and with at least a portion of the capillary tube visible when the housing is in the first position;

a marking on the housing adjacent the capillary tube to indicate a position along the capillary tube that corresponds to a pre-determined amount of biological sample; and a mechanical actuator, configured to dispense the biological sample from the capillary tube as the housing is moved from the first position to the second position, the mechanical actuator further configured to control a plunger disposed within the first portion of the housing to dispense the biological sample from the capillary tube.

15. The device of claim 14, further comprising:

a reagent chamber, disposed within the housing, the reagent chamber holding a liquid reagent, and a second plunger, controlled by the mechanical actuator, and configured to dispense and mix the liquid reagent proportionally with the biological sample internal of the housing.

16. The device of claim 14 wherein at least a portion of the capillary tube remains visible external to the housing when the device is in the second position.

17. A device for collecting a biological sample comprising:

a housing having a collection well formed therein to receive a biological sample;

a conduit, disposed within the housing, the conduit having openings at a first end and a second end, with the opening at the first end receiving the biological sample from the well via capillary action and thereby drawing the biological sample from the well into the conduit;

a sample storage chamber, disposed within the housing, and arranged to receive the biological sample from the conduit;

the housing further configurable in a first position and a second position, whereby the first position provides an opening to the well, and the second position restricts access to the well; and a mechanical actuator, configured to dispense a predetermined amount of the biological sample from the second end of the conduit into the sample storage chamber via mechanical force; and wherein a portion of the conduit remains visible external to the housing when the device is in the second position.

18. The device of claim 17 additionally comprising:

a plunger, disposed within the conduit; and wherein the mechanical actuator is further configured to control the plunger to dispense the biological sample into the sample storage chamber.

19. The device of claim 17 wherein the conduit is a capillary tube.

20. The device of claim 17 further comprising multiple conduits receiving the biological sample from the sample collection well.

21. The device of claim 17 wherein the sample storage chamber holds a reagent.

22. The device of claim 17 wherein the sample storage chamber includes a membrane.

23. The device of claim 17 wherein the membrane further includes a reagent.

24. The device of claim 17 additionally wherein:

the housing is formed from first and second portions configured to be pressed towards one another, to configure the device from the first position to the second position.

25. The device of claim 17 wherein the mechanical actuator is rotatable.

26. The device of claim 24 wherein the first and second portions of the housing are locked in position when the device is moved to the second position.

* * * * *